(12) United States Patent
Messina

(10) Patent No.: US 6,186,967 B1
(45) Date of Patent: Feb. 13, 2001

(54) ELEVATION SUPPORT FOR A LIMB

(76) Inventor: Frank Messina, 24 Cedar Ct., Freehold, NJ (US) 07728

( * ) Notice: Under 35 U.S.C. 154(b), the term of this patent shall be extended for 0 days.

(21) Appl. No.: 08/993,616

(22) Filed: Dec. 18, 1997

(51) Int. Cl.[7] ................. A61F 5/00; A61F 5/37; A47C 20/02
(52) U.S. Cl. ............... 602/23; 602/27; 128/882; 5/648
(58) Field of Search ................ 602/1, 5, 6, 12, 602/13, 15, 23, 27; 128/845, 846, DIG. 20, 877, 882; 5/648, 650, 646, 647; 601/148, 151, 152; 482/111, 112; 441/80, 88, 125, 129

(56) References Cited

U.S. PATENT DOCUMENTS

| | | | |
|---|---|---|---|
| 3,548,819 | * 12/1970 | Davis | 602/14 |
| 4,157,713 | * 6/1979 | Clarey | 602/13 |
| 4,364,135 | * 12/1982 | Emmerich nee Giesche | 602/23 X |
| 4,936,804 | * 6/1990 | Dowdeswell | 441/6 |
| 4,982,745 | * 1/1991 | Shields | 128/877 |
| 5,085,214 | * 2/1992 | Barrett | 128/DIG. 20 X |
| 5,190,489 | * 3/1993 | Yeung | 441/122 |

* cited by examiner

Primary Examiner—Richard J. Apley
Assistant Examiner—Denise Pothier
(74) Attorney, Agent, or Firm—Stroock & Stroock & Lavan LLP

(57) ABSTRACT

An elevation support for elevating a human limb of a patient to a desired elevation, including a body having a longitudinal aperture therethrough and an insertion opening for receiving at least a portion of the limb, wherein the body is shaped and sized so as to permit concomitant rolling motion along a support surface when the patient exerts a rotational force on the body via the inserted limb while maintaining the limb at the desired elevation.

15 Claims, 4 Drawing Sheets

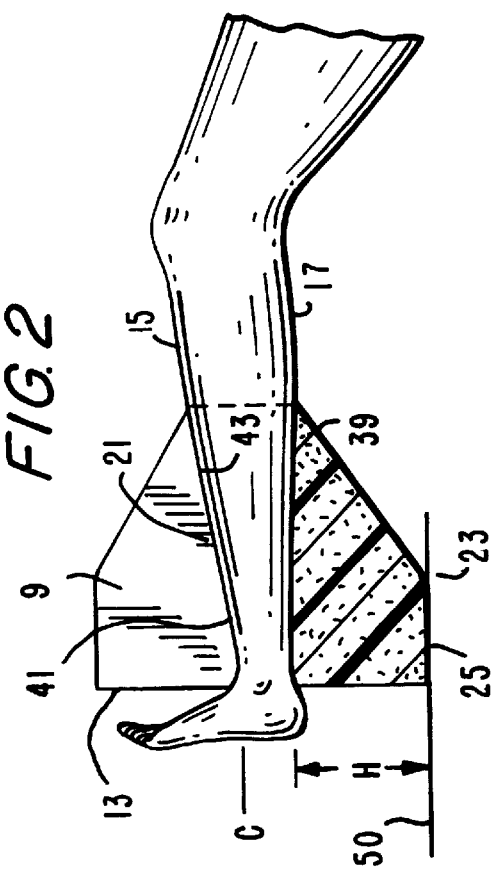
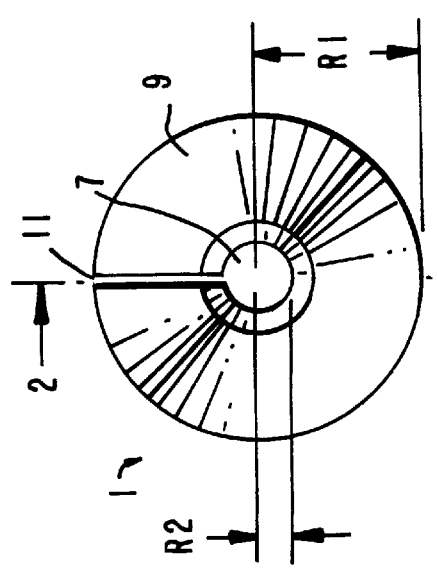
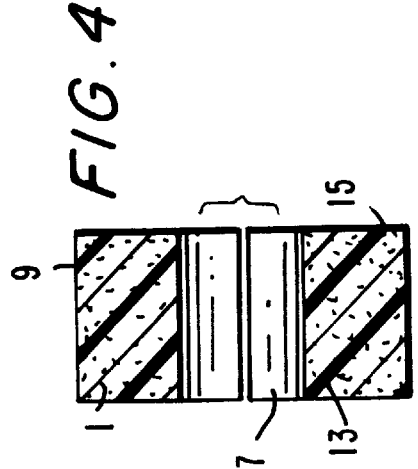
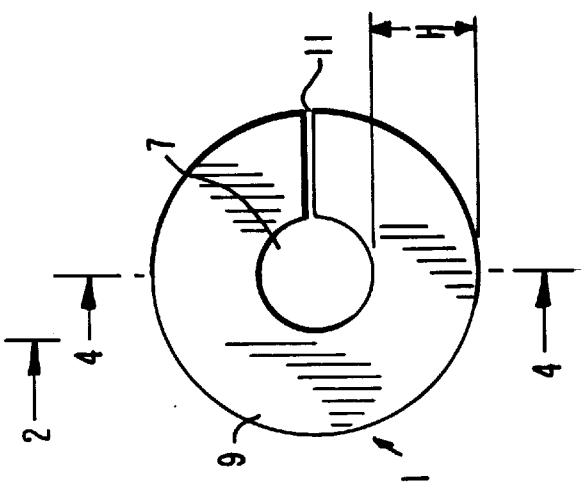

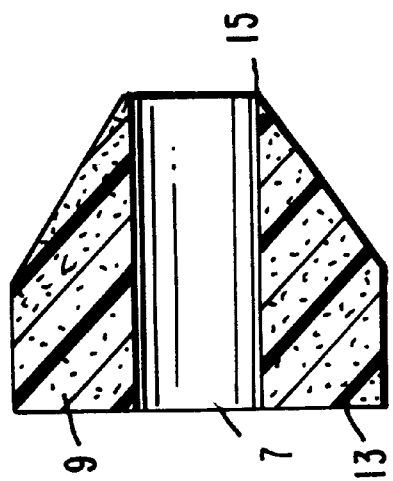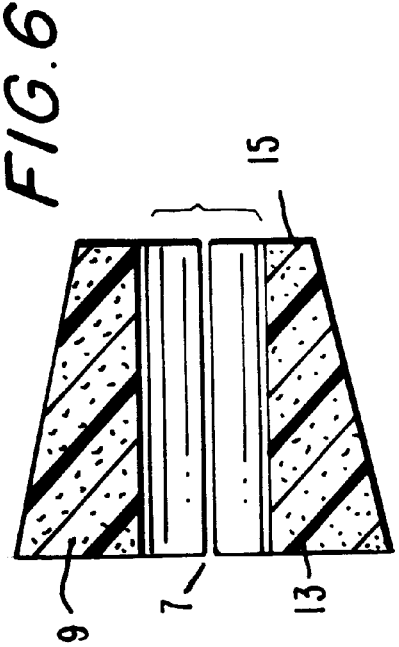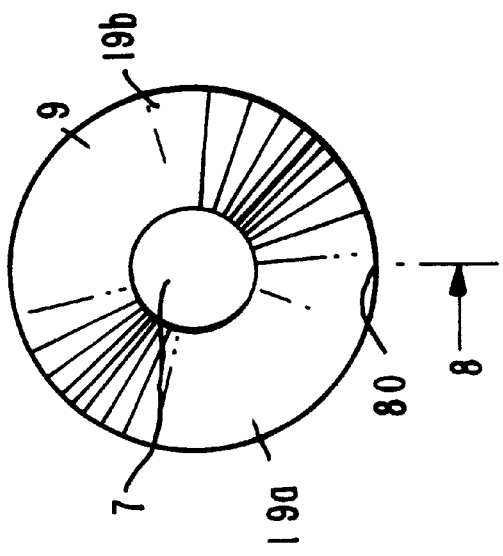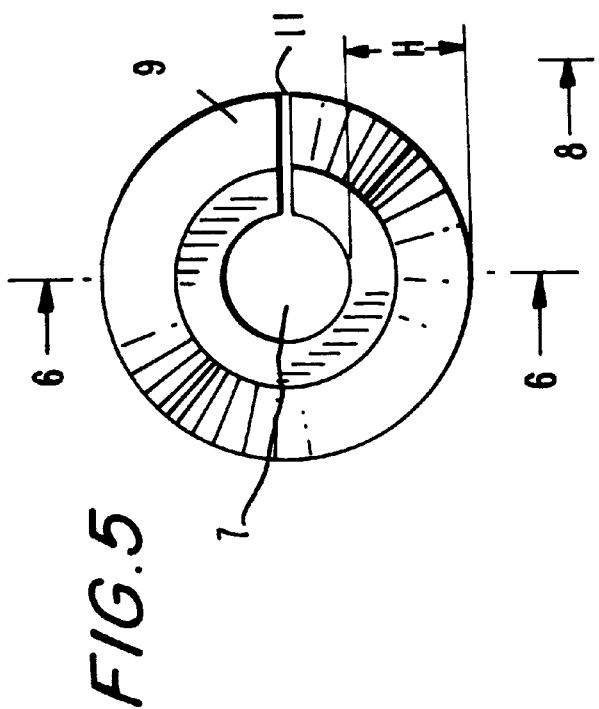

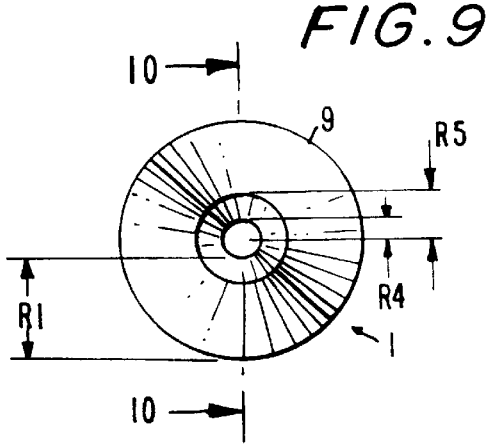
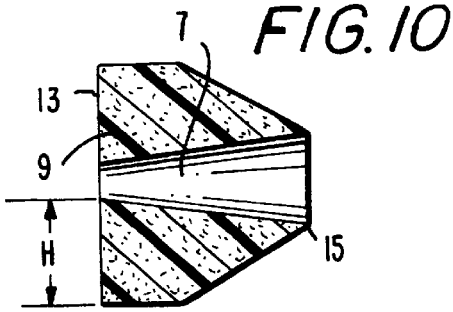
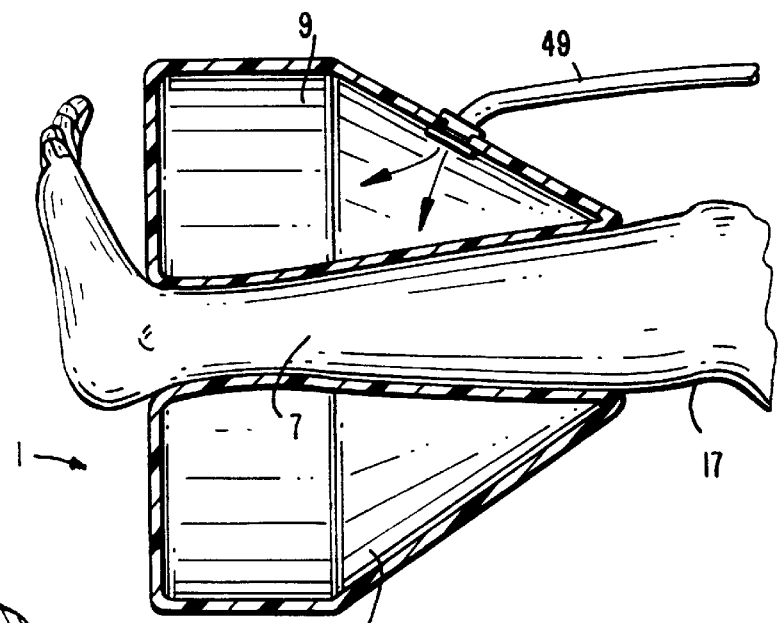
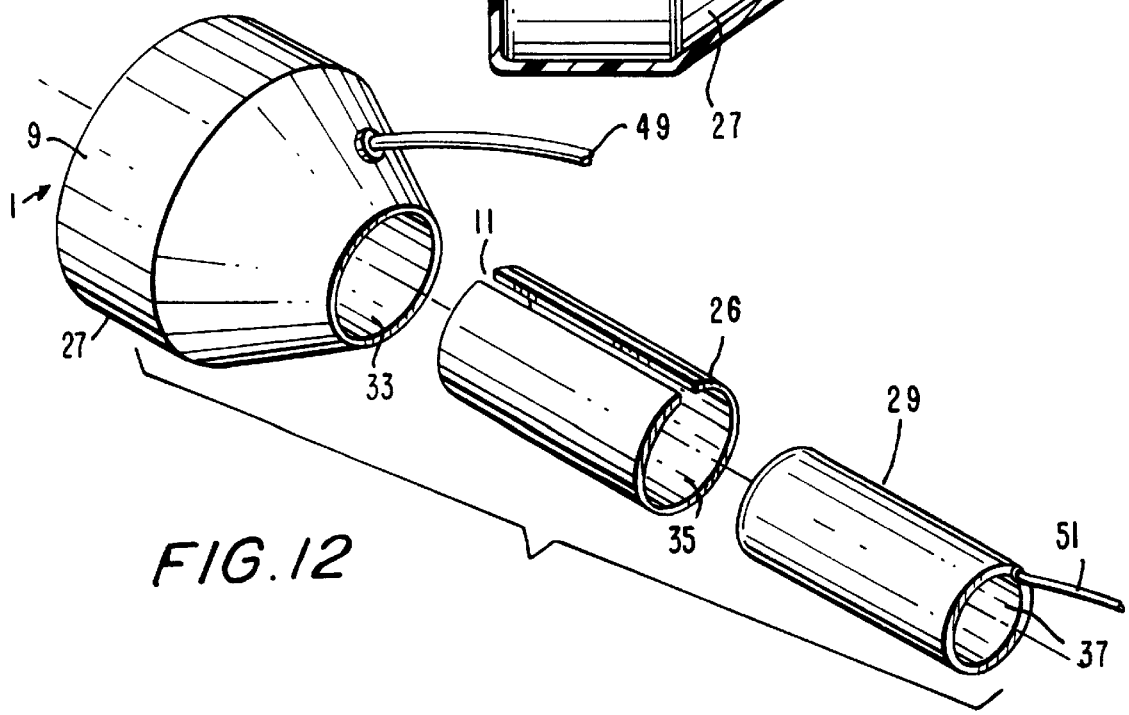

ELEVATION SUPPORT FOR A LIMB

FIELD OF THE INVENTION

This invention relates to an elevation support for elevating a human limb to a desired elevation as part of the recuperative process following an injury to or surgery on the limb or for other therapeutic purposes.

BACKGROUND OF THE INVENTION

The technique of elevating a limb to reduce the swelling and pain resulting from an injury to that limb is widely recognized and accepted. For example, it is recommended that a person recovering from an ankle sprain apply the four R.I.C.E. modalities to speed recovery; i.e. Rest, Ice, Compression and Elevation. Also, elevation of a foot, hand or wrist is often recommended after surgery. Elevation of a limb is therefore an important step in the recuperative process following injury to or surgery on the limb, as well as a wide variety of other therapeutic purposes.

The use of a support to elevate an injured limb is generally known. Prior art elevation supports are generally made of a rectangular or triangular block with a flat base which rests on a support surface, and may also be equipped with a channel cut into its top within which the limb lies. In the case of an injured ankle, for example, a patient lying on their back places the lower portion of his or her limb in the channel, which causes the ankle to be elevated to a desired height or that height recommended by a treating physician, therapists or other healthcare professional, as dictated by the geometry of the block. Elevation of the ankle aids in the recovery from an ankle injury by preventing the buildup of blood and fluids which can often result in painful swelling.

While the prior art elevation supports work for their intended purposes, a significant drawback to these prior art devices is that they prohibit movement, thus making them uncomfortable for long-term use. For the same reason, prior art devices are also quite difficult for the patient to use while sleeping. Additionally, because the patient's limb is not secured to the elevation support, but merely lies in an open channel, the limb can easily fall out of the channel should the patient attempt to change positions. This results in the patient's limb no longer being elevated, and possibly causing painful jarring of the limb. The present invention is directed at overcoming inadequacies in the prior art.

SUMMARY OF THE INVENTION

The present invention provides an elevation support for elevating a human limb to a desired therapeutic elevation. The support is intended to rest upon a support surface, e.g. a bed, sofa, mat, or any other generally horizontal surface capable of supporting the user, while the user of the device lies supine on the same or an adjacent support surface. The support consists of a body with a longitudinally extending aperture therethrough and an opening so that the limb may be easily inserted into, yet comfortably retained, in the aperture. The aperture comprises a portion that is predeterminately sized and shaped so as to resiliently grip at least a portion of the inserted limb, in typical use the ankle, calf, foot, wrist, hand and/or forearm; depending on the application to which it is applied. The body of the support is so shaped and sized as to permit the outer surface of the body to concomitantly assume a rolling motion along the support surface when the user exerts a rotational force on said body via said gripped limb portion, as when the user attempts to roll over into different positions while supine. In this way, the patient is not restricted to a single supine position while using the support, but rather the device permits the user to move into a variety of positions, while the desired elevation is maintained throughout the range of motion.

The body is preferably constructed of a resilient material, predeterminately sized and shaped so as to accommodate different limb sizes and to firmly grip the limb while the person using the support changes positions. The body has a front end, referring to that portion of the support where the limb extends into the device, and a back end, referring to that portion where the hand or foot extends out from the support. The body is preferably frustroconically shaped from a point offset from the back end of the body to the front end of the body, and preferably cylindrically shaped from the back end to the point offset from the back end. The difference between the largest outside diameter of the body and the diameter of the aperture at that portion of the aperture where the limb is retained can be readily designed, depending on the needs and physical characteristics of the user, such that the limb is elevated to a desired therapeutic elevation. Moreover, because both a frustroconical solid and a cylinder are readily rolled along their outer circumference when an axial rotational force is applied, the user's limb may be rotated with minimal force and discomfort. Indeed, the desired elevation is maintained even while the user moves through a variety of supine positions. Also, the cylindrically shaped body portion reduces the tendency of the elevation support to tilt forward toward the user, reducing pressure on the limb and discomfort to the user. Thus, the body's shape and size provides the body with the ability to roll concomitantly with the inserted limb as the person's limb rotates during movement or a change in position by the user, while elevation is maintained throughout the user's range of motion.

Alternatively, as a matter of design choice, the body may be frustroconically shaped from the back end of the body to the front end, or the body may be cylindrically shaped from the back end to the front end.

Preferably, the longitudinal aperture or bore formed in the body is cylindrical or tube-shaped from the back end of the body to a point offset from the back, and conical or outwardly sloped from the point offset from the back end to the front end of the body. The advantage of the aperture being so shaped is that the tube-shaped section increases the amount of surface area of the aperture wall that is in contact with the limb, thereby providing a firm grip on the limb, while the sloped section of the aperture enables the limb to lie in a more natural, sloped position thereby increasing the comfort to the patient.

Alternatively, the aperture may be entirely tube shaped to maximize the surface area of the aperture wall that is in contact with the limb so that the limb is more firmly gripped. Or, the bore can be sloped from the back end to the front end of the body, thereby minimizing pressure on the limb so that patient comfort is maximized.

Also, the elevation support may be constructed using an inflatable shell, or multiple shell portions, having the same size and shape characteristics described above. Or, the inflatable shell may comprise a supportive frame bearing inflatable sections that when inflated assume shapes and sizes that provide the features described above. The supportive frame may be configured with a hollow portion having an insertion slit extending along its outer surface in the longitudinal direction. An inflatable insert may be located in the hollow portion of the frame and inflated so that the elevation support firmly and comfortably grips the limb. The inflatable insert may also be comprised of multiple sections, each inflatable to a different shape.

It is thus an object of this invention to provide an improved limb support for a user desiring to elevate a limb while retaining the ability to move.

Other objects and features of the present invention will become apparent from the following detailed description, considered in conjunction with the accompanying drawing figures. It is to be understood, however, that the drawings, which are not to scale, are designed solely for the purpose of illustration and not as a definition of the limits of the invention, for which reference should be made to the appended claims.

BRIEF DESCRIPTION OF THE DRAWINGS

In the drawing figures, which are not to scale, and which are merely illustrative, and wherein like reference numerals depict like elements throughout the several views:

FIG. 1 is an front elevational view of an elevation support constructed in accordance with a preferred embodiment of the present invention.

FIG. 2 is a side view taken along section 2—2 of FIG. 1, showing an exemplary inserted limb.

FIG. 3 is a front elevational view of an alternative embodiment of the elevation support constructed in accordance with the present invention.

FIG. 4 is a side sectional view taken along section 4—4 of FIG. 3.

FIG. 5 is an elevational view of another alternative embodiment of the elevation support constructed in accordance with the present invention.

FIG. 6 is a sectional view taken along section 6—6 of FIG. 5.

FIG. 7 is an elevational view of another alternate embodiment of the elevation support constructed in accordance with the present invention.

FIG. 8 is a sectional view taken along section 8—8 of FIG. 7.

FIG. 9 is an elevational view of another alternate embodiment of the elevation support constructed in accordance with the present invention.

FIG. 10 is a sectional view taken along section 10—10 of FIG. 9.

FIG. 11 is an elevation support constructed from an inflatable shell.

FIG. 12 is an exploded perspective side view of another alternate embodiment of the elevation support constructed in accordance with the present invention.

DETAILED DESCRIPTION OF THE PREFERRED EMBODIMENTS

Figure 13:
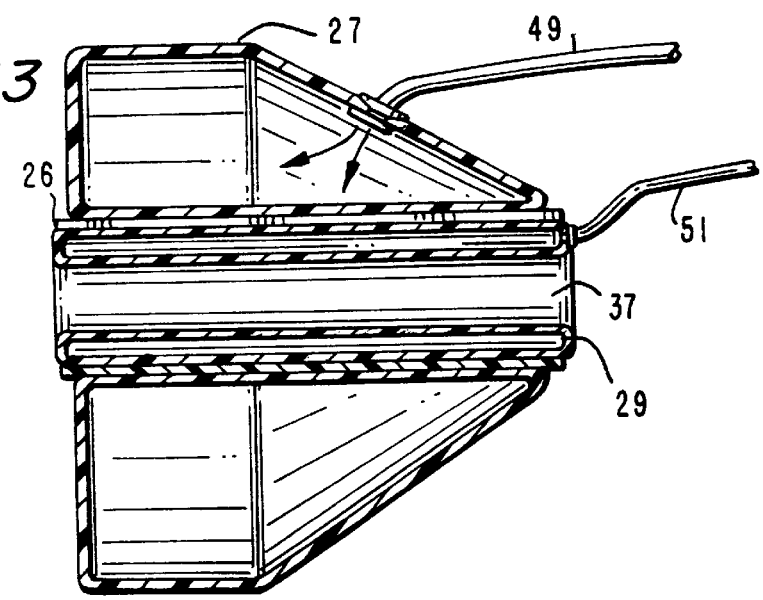
FIG. 13 is a side sectional view of the elevation support of FIG. 12.

Referring first to the FIGS. 1 and 2, there is shown an elevation support 1 constructed in accordance with a preferred embodiment of the present invention. Elevation support 1 consists of a body 9 having a longitudinal bore or aperture 7 extending axially therethrough and an insertion opening defined as a slit 11 through which, by opening the slit as further defined below, a user's limb 17 may be easily inserted into, and retained in, support 1. As used herein the term user means a person using the device as described herein. The term limb is intended to interchangeably mean an arm or leg of a user, and the use of either as an example should be interpreted to include the other.

Body 9 is preferably formed of a light weight, resilient, flexible material, such as foam rubber, but may also be constructed from some other resilient, moldable material, such as a plastic, plastic foam, a flexible, impact absorbing gel, e.g. SORBOTHANE, a fluid-filled container, or other art recognized equivalent material, provided the chosen material, or combination of materials, renders body 9 sufficiently resilient to permit comfortable retention of the limb within the aperture while substantially maintaining the overall shape of the body to accomplish the functions described hereinbelow.

As further described below, body 9 is predeterminately sized and shaped so as to accommodate limbs of different sizes and to easily roll along its outer surface when a limb retained therein is turned, while aperture 7 is predeterminately sized and shaped to resiliently grip the inserted limb as a user rotates the limb when in motion.

Specifically, aperture 7 includes a generally cylindrical, tube-shaped retaining section 41 extending from a back end 13 of body 9 to a point 21 in aperture 7. The length and diameter of retaining section 41 is such that sufficient surface area of the inner wall of aperture 7 in body 9 is in contact with limb 17 so that body 9 firmly grips inserted limb 17. Because body 9 is resilient, the gripping of limb 17 in retaining section 41 is strong enough for the limb to be gripped while a user is rotating an inserted limb, yet yielding enough not to cause discomfort or impede blood circulation within the limb 17. Retaining section 41 is thus predeterminately sized and shaped according to the particular user and the particular limb that will be inserted. Retaining section 41 may accordingly be made in a variety of sizes, depending on the needs of the user. Also, it should be recognized that retaining section 41 can be sized to accommodate a cast or splint placed on the inserted limb (not shown), the section 41 gripping the cast or splint rather than leg 17 directly.

Aperture 7 also includes a sloped section 43 which extends from point 21 to front end 15, the diameter of sloped section 43 increasing from point 21 to front end 15. The sloped section 43 is sized and shaped such that inserted limb 17 will be comfortably supported within sloped section 43 in accordance with the actual shape of limb 17. This shape is more natural for inserted limb 17 of a user lying in a horizontal position, resulting in less pressure being exerted on limb 17 during use and increased comfort to the patient.

The actual size and shape of the sloped section 43 and retaining section 41 of aperture 7 may be varied so that retaining section 41 extends a greater axial distance through body 9, to increase the retaining area, and/or sloped section 43 of aperture 7 can have a diameter such that sloped section contributes to the retention of limb 17. Alternatively, the change in diameter of sloped section 43 can be adjusted such that a portion of sloped section 43 retains a portion of limb 17, while the remainder of sloped section 43 is larger than the outer diameter of limb 17, as matter of design choice, depending on the needs of the user and the size of the inserted limb. Moreover, the axial length of aperture 7, and likewise of body 9, may be made sufficiently long to have inserted therein as much of limb 17 as is therapeutically desirable.

Body 9 preferably includes a generally frustroconical (the frustum of a right circular cone) portion 39 extending from a point 23 on the outer surface of body 9 to the front end 15 of body 9. Body 9 also preferably includes a generally cylindrical portion 25 extending from point 23 to the back end 13 of body 9 to provide stability to elevation support 1 while a user is supine and while support 1 is supported on a support surface 50. This reduces the likelihood that elevation support 1 will tilt forward towards front end 15 which would exert pressure on limb 17 causing patient discomfort. However, because a cylinder and a frustroconical solid are readily rolled on their respective outer surfaces when an rotational force is applied, elevation support 1 will readily roll concomitantly with inserted limb 17 as a user rotates limb 17 during a change in position. Also, support 1 will roll regardless of whether the outer surface of cylindrical portion 25 or the frustroconical portion 39 contacts the support surface. Because body 9 is preferably resilient, it is contemplated that both static support and rolling motion be achieved while either one, or both, or parts of both of the portions 25 and 39 of body 9 contact support surface 50.

To achieve the desired elevation of limb 17 while inserted in aperture 7, body 9 is dimensioned so that the difference between the radius R1 of cylindrical portion 25 of body 9 and the radius R2 of retaining section 41 of aperture 7 is such that inserted limb 17 of a user lying in a generally horizontal position is elevated to a desired therapeutic height H.

In use, a user or patient inserts limb 17 into aperture 7 through insertion slit 11. Because body 9 is made of a resilient material such as foam rubber, body 9 may be deformed at insertion slit 11 to such an extent that slit 11 widens into a channel of sufficient size to insert limb 17 into aperture 7. Alternatively, as seen in FIG. 7, body 9 may be formed of two sections 19 and 19a and hinged via hinge 80 to accommodate opening of body 9 and insertion of limb 17 while body 9 is open (not shown). Alternatively, body 9 may be resilient enough to permit elimination of slit 11, a user instead inserting limb 17 directly into aperture 7 from front end 15.

Once inserted into support 1, limb 17 lies in aperture 7 in a longitudinal direction within body 9 along an axis of rotation C of body 9. When a user is lying supine with limb 17 inserted in aperture 7, and support 1 is resting on support surface 50, limb 17 is elevated to desired height H. As the patient rotates limb 17, such, for example, as during a change in position, a rotational force is exerted upon body 9 by limb 17 along axis of rotation C. Elevation support 1 accordingly rotates concomitantly with limb 17 while maintaining limb 17 at desired elevation height H.

Further, because body 9 is constructed from resilient material, retaining section 41 will elastically enclose that portion of inserted limb 17 that is within retaining section 41, thereby holding limb 17 securely in aperture 7 as patient rotates limb 17 while changing positions. Also, resilient body 9 offers a modicum of protection from jarring and bumping during movement.

In an exemplary embodiment, the length of body 9 between front end 15 and back end 13 may be approximately 9 inches, while R2 is approximately 1.5 inches and R1 is approximately 7 inches, yielding a height H of approximately 5.50 inches. The axial length of retaining section 41 extends between point 23 and back end 13 approximately 3 inches, while the radius of sloped portion 43 varies from approximately 1.5 inches to approximately 2.5 inches. As mentioned above, and as will be readily recognized by the person of skill in the art utilizing the teachings herein, the various dimensions described herein are exemplary, and may be readily modified and adapted to suit a wide variety of users, limb lengths, limb sizes and shapes, and therapeutic elevations. Thus a wide variety of shapes are contemplated and readily realized, making the support particularly suited to mass production as well as customization. Nonetheless, the specific dimensions by which any particular application is satisfied is a matter of application specific design choice.

Moreover, there exists alternate contemplated embodiments which also provide the benefits of the present invention. Referring now to FIGS. 3 and 4, there is shown an elevation support 1 constructed according to an alternate embodiment of the present invention. As described above, body 9 is made from a resilient material and has aperture 7 and insertion slit 11, although insertion slit 11 may be eliminated, or substituted with hinge 80, as described above. In this embodiment, however, the outer surface of body 9 is cylindrically shaped from back end 13 to front end 15. Body 9, when completely cylindrically shaped, provides added stability to elevation support 1 in that the body 9 will resist movement towards front end 15 caused by the weight of inserted limb 17 which might otherwise cause elevation support 1 to tilt toward front end 15. Reducing the likelihood that the elevation support will tilt reduces the pressure body 9 may exert on limb 17 and thereby increases the comfort to the patient. Moreover, aperture 7 may be entirely cylindrical, as best seen in FIG. 4, or comprised of two sections as shown in FIGS. 1 and 2 as described above, or fully sloping as shown in FIG. 10 as described further hereinbelow.

Referring now to FIGS. 5 and 6, there is shown yet another contemplated embodiment of the present invention. As with the previous embodiments, elevation support is constructed of resilient material having aperture 7 and, optionally, insertion slit 11. However, in this embodiment, body 9 is frustroconically shaped from back end 13 to front end 15. The difference between the radius of body 9 measured at back end 13 and the radius of aperture 7 measured at back end 13 is such that inserted limb 17 is elevated to the desired therapeutic height H. Because a frustroconical solid is readily rolled on its outer circumference when an axial rotational force is applied to it, the rotational resistance of body 9 is minimized thereby enabling elevation support 1 to easily roll as limb 7 is rotated while the user changes positions. As above, aperture 7 may be sized and shaped in accordance with any of the embodiments depicted in FIGS. 2, 6, or 10.

Referring now to FIGS. 7 and 8, there is shown another alternate embodiment of the present invention. In this embodiment, body 9 may be shaped as described above in connection with FIGS. 1 and 2, however aperture 7 maintains an equal radius along its axial length from back end 13 to front end 15. The advantage of having aperture 7 fully cylindrically shaped is that an increased portion of the surface area of body 9 will be in contact with inserted limb 17 thereby maximizing the grip body 9 has on limb 17.

Referring now to FIGS. 9 and 10, there is shown another alternative embodiment of the present invention. In this embodiment, body 9 may be shaped as described above in connection with FIGS. 1 and 2, or in accordance with any of the previously described embodiments. However, aperture 7 is fully sloped, extending outward from back end 13 to front end 15. In other words radius R4 of aperture 7 at back end 13 increases to radius R5 as measured at front end 15, such that inserted limb 17 is gripped proximate back end 13 and merely rests in aperture 7 proximate front end 15. Also, the difference between radius R1 of body 9 measured at back end 13 and radius R4 of aperture 7 measured at back end 13 is such that inserted limb 17 is elevated to the desired therapeutic height H. The slope of aperture 7 is such that limb 17 of a user lying in a horizontal position will be comfortably supported in aperture 7 with minimal pressure exerted on limb 17 by body 9 even as limb 17 rotates.

Referring now to FIG. 11, body 9 of elevation support 1 is depicted as constructed from an inflatable shell 27. Inflatable shell 27, when inflated, is depicted having a shape and dimension as shown and described in connection with FIGS. 1 and 2 above, it being recognized however that inflatable shell 27 may be configured to yield a body 9 and aperture 7 having the size and shape of any combination of the embodiments described above, thereby providing the aforementioned benefits. Referring again to FIG. 11, inflatable shell 27 contains aperture 7 therethrough that is of a shape and dimension as that shown and described in connection with FIG. 2, it being recognized however that inflatable shell 27 may be configured to yield an aperture in accordance with any of the previously described embodiments.

To use elevation support 1 according to this embodiment, a user inserts limb 17 through aperture 7 while inflatable shell 27 is deflated. When limb 17 is inserted into aperture 7, inflatable shell 27 is inflated via an inflation tube 49 so that inflatable shell 27 firmly grips limb 17, permitting shell 27 to rotate concomitantly with limb 17. A benefit of constructing elevation support 1 with an inflatable shell is that support 1 can be inflated to different pressures and thus be readily adapted to fit different limb sizes and elevations.

Referring now to FIGS. 12 and 13, there is shown another alternate embodiment of the present invention. In this embodiment, inflatable shell 27 forms the exterior of elevation support 1. Inflatable shell 27, when inflated, is of a shape and dimension of any of the embodiments described above, although it is depicted herein in accordance with the embodiment of FIG. 2 for purposes of example. Inflatable shell 27 has a longitudinal aperture 33 therethrough for inserting a supportive frame 26. Frame 26 is a hollow, elastically deformable tube, preferably made of plastic, having an insertion slit 11 extending along the longitudinal direction. Frame 26 may accordingly be made of a material that is resilient yet elastically flexible so that insertion slit 11 may be opened to permit limb 17 to be inserted into hollow portion 35 while at the same time be sturdy enough to reliably hold limb 17 within it, while also maintaining its shape to sufficiently support inflatable shell 27.

An inflatable insert 29 is located in hollow portion 35 of frame 26. Inflatable insert 29 has an aperture 37 therethrough for inserting limb 17. Aperture 37 of inflatable insert 29 is shaped so that, when inflated via inflation tube 49, inflatable insert 29 firmly grips limb 17 and provides maximum comfort by reducing unnecessary pressure on patient's limb 17. Such shapes, for example, may include any of the aperture shapes described in the embodiments discussed above. Also, inflatable insert 29 may be selectively inflated for adjusting elevation support to firmly grip limbs of different sizes. Moreover, inflatable shell 27 and/or inflatable insert 29 may also be configured with insertion openings (not shown) providing the functionality of insertion slit 11.

Figure 14:
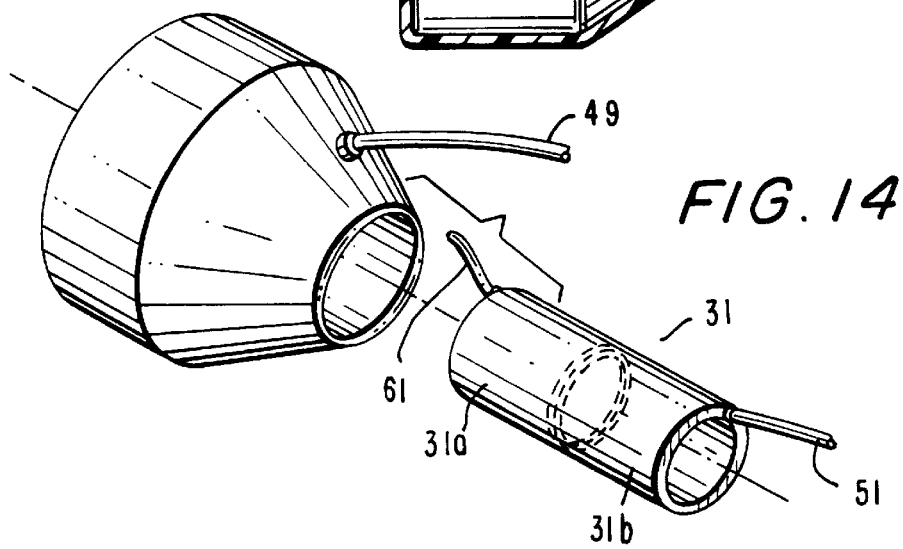
FIG. 14 is an exploded perspective view of another alternate embodiment of the elevation support constructed in accordance with the present invention.
Figure 15:
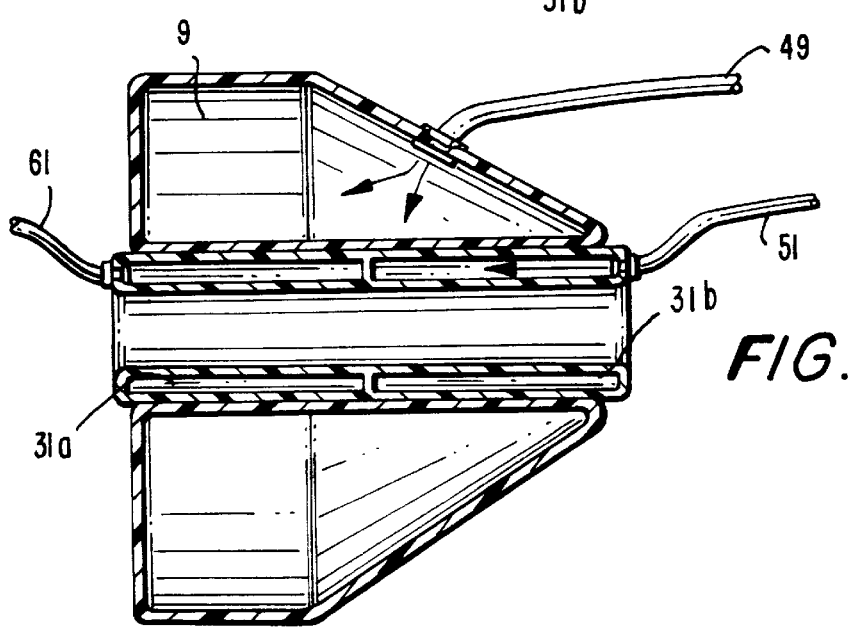
FIG. 15 is a side sectional view of the elevation support of FIG. 14.

Referring now to FIGS. 14 and 15, support 1 may also be configured using a two-part inflatable insert 31, with each part thereof being separately inflatable. The two parts may be a back inflatable insert part 31a and a front inflatable insert part 31b. Back inflatable insert part 31a and front inflatable insert part 31b may be attached together or be fully separate, but are preferably separately inflatable via rear tube 61 and front tube 51 respectively. Supportive frame 26 may also optionally be used, although not shown in FIGS. 14 and 15. In this embodiment, back inflatable part 31a forms the retaining part, and may be inflated to a degree which provides comfortable retention, while front inflatable part 31b may be inflated to a lesser degree, providing comfortable support.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. For example, it is contemplated that the scope of the invention encompasses any number of combinations of body shapes and sizes combined with any number of shapes and sizes of apertures to yield supports of varied geometries for varied applications. Further, multiple combinations of materials are contemplated, such as, by way of non-limiting example, resilient bodies with single or multi-part inflatable inserts, or inflatable bodies with resilient apertures of varied geometries, both of the types described herein and as further derived by the person of skill as a matter of application specific design choice. It is the intention, therefore, to be limited only as indicated by the scope of the claims appended hereto.

I claim:

1. A support for elevating a limb of a patient, comprising:
    a body having a centrally aligned, longitudinally oriented, elongated aperture extending therethrough;
    an insertion opening for permitting insertion of at least a portion of the limb into said aperture;
    said aperture comprising a gripping portion that is predeterminately sized and shaped so as to resiliently grip at least a portion of the inserted limb; and
    said body comprising a frustroconical front portion and a cylindrical back portion, a first radius measured at a first end of said front portion and a second radius measured at a second end of said front portion, said back portion having a cylinder radius substantially equal to said second radius, said body being so shaped and sized as to maintain the limb at a desired elevation and to permit concomitant rolling motion along a support surface when the patient exerts a rotational force on said body through rotation of the resiliently gripped portion of the limb.

2. The support of claim 1, wherein said aperture is cylindrically shaped.

3. The support of claim 2, wherein said aperture further complises a flared portion having a radius that increases as measured in a direction extending outwardly from said second end towards said first end of said front portion.

4. The support of claim 2, wherein said aperture further comprises an inside radius measured at said back portion such that the difference between said cylinder radius and said inside radius is equal to said desired elevation.

5. The support of claim 2, wherein said body is inflatable.

6. The support of claim 1, wherein said aperture further comprises:
    a cylindrical portion extending through said back portion of said body, said cylindrical portion being dimensioned so as to be in gripping contact with at least a portion of the inserted limb; and
    a flared portion extending through said front portion and having a radius that increases as measured in a direction extending away from said back portion.

7. The support of claim 1, wherein said body is constructed from a light weight, resilient, flexible material so as to permit the comfortable retention of said limb in said aperture while substantially maintaining the shape of said body.

8. The support of claim 1, wherein said desired elevation is in the range of five inches to seven inches.

9. The support of claim 1, wherein said body further comprises a fluid filled insert positioned within at least a portion of said aperture.

10. The support of claim 1, wherein said insertion opening comprises said aperture.

11. A support for elevating a limb of a patient to a desired elevation, comprising:

an inflatable insert having a longitudinally oriented, elongated aperture extending therethrough, said aperture comprising, when said insert is inflated, a gripping portion that is sized and shaped so as to resiliently grip at least a portion of an inserted limb of the patient;

an inflatable shell having a longitudinally oriented, centrally aligned elongated bore extending therethrough for receiving said inflatable insert, said inflatable shell having a frustroconical first portion and a cylindrical second portion, said cylindrical portion having a cylinder radius equal to the greatest radius of said frustroconical portion, said shell being so sized and shaped when inflated as to maintain the inserted limb at a desired elevation and to permit concomitant rolling motion along a support surface when the patient exerts a rotational force on said shell through the resiliently gripped portion of the limb.

12. The support of claim 11, further comprising a cylindrical hollow supportive frame for receiving said inflatable insert, said supportive frame and inflatable insert being inserted into said bore of said inflatable shell so as to provide support for said inflatable shell.

13. The support of claim 12, wherein said inflatable insert further comprises a back inflatable portion and a front inflatable portion, and wherein said back inflatable portion may be inflated to a first pressure so as to firmly grip the limb while said front inflatable portion may be inflated so as to comfortably support the limb.

14. The support of claim 12, wherein said aperture of said inflatable insert further comprises an inside radius measured at a point adjacent said cylindrical second portion such that the difference between said inside radius and said cylinder radius is equal to said desired elevation.

15. The support of claim 12, wherein said desired elevation is in the range of five inches to seven inches.

* * * * *